(12) United States Patent
Masaki (10) Patent No.: US 10,194,786 B2
(45) Date of Patent: Feb. 5, 2019

(54) INSERTION DEVICE

(71) Applicant: Olympus Corporation, Tokyo (JP)

(72) Inventor: Yutaka Masaki, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 100 days.

(21) Appl. No.: 14/479,810

(22) Filed: Sep. 8, 2014

(65) Prior Publication Data

US 2015/0045621 A1 Feb. 12, 2015

(51) Int. Cl.
| | | |
|---|---|---|
| A61B 1/00 | (2006.01) |
| A61B 1/005 | (2006.01) |
| A61B 1/05 | (2006.01) |
| A61M 25/01 | (2006.01) |
| F16D 11/00 | (2006.01) |

(52) U.S. Cl.
CPC .......... *A61B 1/0051* (2013.01); *A61B 1/0016* (2013.01); *A61B 1/0052* (2013.01); *A61B 1/0057* (2013.01); *A61B 1/05* (2013.01); *A61M 25/0136* (2013.01); *A61M 25/0147* (2013.01); *F16D 11/00* (2013.01)

(58) Field of Classification Search
CPC .................................................. A61B 1/0052
USPC ....................................... 600/146, 147, 152
See application file for complete search history.

(56) References Cited

U.S. PATENT DOCUMENTS

| 5,007,406 A * | 4/1991 | Takahashi ................. B25J 1/02 |
| | | 600/119 |
| 8,303,487 B2 | 11/2012 | Ueno et al. |
| 2004/0073084 A1 * | 4/2004 | Maeda ................. A61B 1/0016 |
| | | 600/101 |
| 2004/0267093 A1 * | 12/2004 | Miyagi .............. A61B 1/00039 |
| | | 600/146 |
| 2007/0232856 A1 | 10/2007 | Ueno et al. |
| 2008/0312503 A1 | 12/2008 | Masaki |
| 2009/0076330 A1 * | 3/2009 | Ashida ................. A61B 1/0052 |
| | | 600/146 |

(Continued)

FOREIGN PATENT DOCUMENTS

| JP | A-02-161928 | 6/1990 |
| JP | A-02-164332 | 6/1990 |
| JP | A-04-210039 | 7/1992 |

(Continued)

OTHER PUBLICATIONS

Aug. 20, 2015 International Preliminary Report on Patentability issued in International Application No. PCT/JP2014/052625.

(Continued)

*Primary Examiner* — Alexandra L Newton
*Assistant Examiner* — Rynae Boler
(74) *Attorney, Agent, or Firm* — Oliff PLC (57) ABSTRACT

An insertion device includes a first rotating member, and a second rotating member coaxially arranged with a rotational axis of the first rotating member and rotating about the rotational axis to bend a bending section. The insertion device includes a moving member arranged inside the first rotating member and the second rotating member along the rotational axis and being movable between a state where an electrical driving force is transmitted to the second rotating member and a state where the electrical driving force is not transmitted to the second rotating member.

12 Claims, 6 Drawing Sheets

(56) References Cited

U.S. PATENT DOCUMENTS

2010/0268031 A1    10/2010    Koyama
2012/0302829 A1*   11/2012    Omoto ................ A61B 1/0052
                                                             600/109

FOREIGN PATENT DOCUMENTS

| JP | H04-256724 A | 9/1992 |
| JP | A-11-32977 | 2/1999 |
| JP | A-2008-307331 | 12/2008 |
| JP | A-2012-100926 | 5/2012 |
| WO | WO 2006/059722 A1 | 6/2006 |
| WO | WO 2010/047223 A1 | 4/2010 |
| WO | WO 2012/074013 A1 | 6/2012 |

OTHER PUBLICATIONS

International Search Report issued in International Patent Application No. PCT/JP2014/052625 dated Apr. 1, 2014 (with translation).
Nov. 28, 2016 Extended European Search Report issued in European Application No. 14749477.7.
Office Action dated Nov. 8, 2017 in Chinese Patent Application No. 201480002680.9.

* cited by examiner

INSERTION DEVICE

CROSS-REFERENCE TO RELATED APPLICATIONS

This is a Continuation application of PCT Application No. PCT/JP2014/052625, filed Feb. 5, 2014 and based upon and claiming the benefit of priority from prior Japanese Patent Application No. 2013-020726, filed Feb. 5, 2013, the entire contents of which are incorporated herein by reference.

BACKGROUND OF THE INVENTION

1. Field of the Invention

The present invention relates to an insertion device wherein a bending section is provided in an inserting section, and the bending section is bendable in first bending directions perpendicular to a longitudinal axis and in second bending directions perpendicular to a longitudinal axis and the first bending directions.

2. Description of the Related Art

International Publication No. 2012/074013 discloses an endoscope which is an insertion device, wherein a bending section is provided to an inserting section, and the bending section is bendable in bending LR directions (first bending directions) perpendicular to a longitudinal axis and in bending UD directions (second bending directions) perpendicular to a longitudinal axis and the first bending directions. In this endoscope, a bending operation knob which acts as a manual bending operating section is coupled to a held section casing of a held section, the held section being provided to the proximal end side of an inserting section. Furthermore, a bending operation dial which acts as an electric bending operating section is coupled to the held section casing.

In this endoscope, a motor which acts as a driving member is driven by inputting an electric bending operation with the bending operation dial. Upon driving the motor, an electrical driving force from the motor is transmitted to a first rotating member which is a sprocket, etc. provided inside the held section casing, and the first rotating member rotates. Thus, one of first linear portions, such as bending wires, etc. which are extended inside the inserting section, is pulled, and the bending section is bent toward one of the bending LR directions. Furthermore, upon inputting a manual bending operation at the bending operation knob, a manual driving force from the bending operation knob is transmitted to a second rotating member, such as a sprocket, etc. provided inside the held section casing, and the second rotating member rotates. Thus, one of second linear portions, such as bending wires, etc. which are extended inside the inserting section, is pulled, and the bending section is bent toward one of the bending UD directions.

BRIEF SUMMARY OF THE INVENTION

An insertion device includes that: an inserting section which is extended along a longitudinal axis; a bending section which is provided to the inserting section, and which is bendable in first bending directions and in second bending directions which are different from the first bending directions; a first rotating member which is configured to rotate to bend the bending section toward one of the first bending directions; a driving member which is configured to generate an electrical driving force upon being supplied with an electric power; an actuating unit which is configured to be actuated upon transmitting the electrical driving force generated in the driving member to the actuating unit; a second rotating member which is coaxially arranged with a rotational axis of the first rotating member, and which is configured to rotate about the rotational axis to bend the bending section toward one of the second bending directions; and a moving member which is arranged inside the first rotating member and the second rotating member along the rotational axis, and which is movable between a state where the electrical driving force is transmitted to the second rotating member while the moving member is connected to the actuating unit and a state where the electrical driving force is not transmitted to the second rotating member while the moving member is not connected to the actuating unit.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION (First Embodiment)

Figure 1:
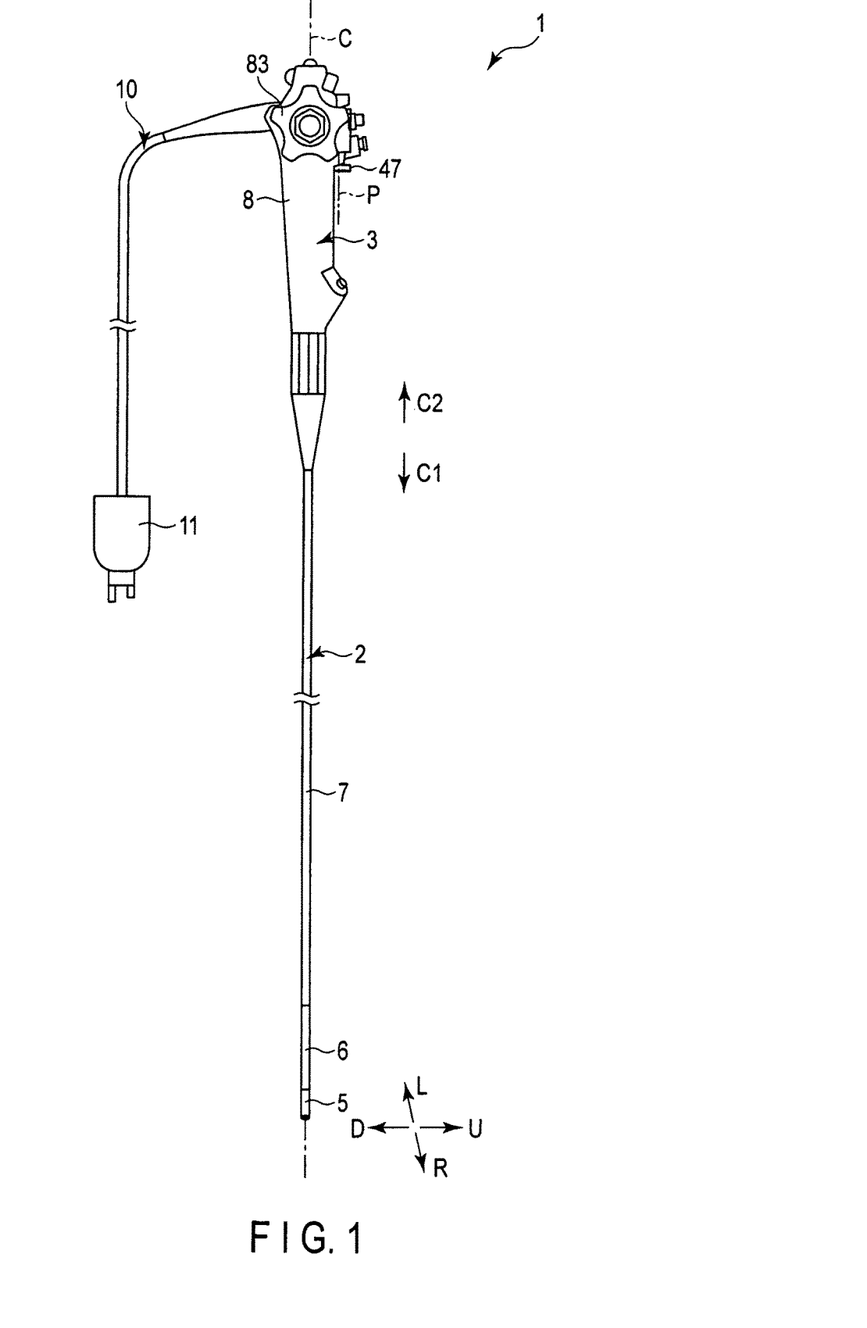
FIG. 1 is a schematic diagram of an endoscope according to the first embodiment of the present invention.
Figure 2:
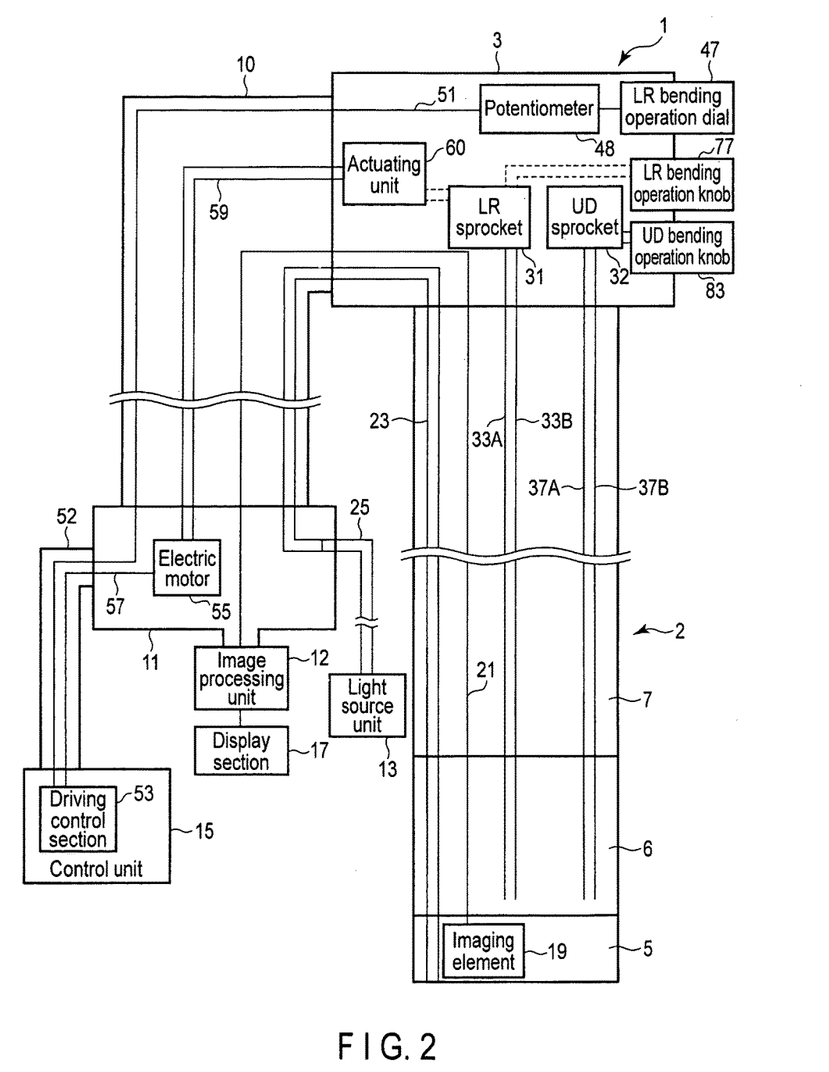
FIG. 2 is a block diagram schematically showing a system in which the endoscope according to the first embodiment is adopted.

The first embodiment of the present invention will be explained with reference to FIG. 1 to FIG. 7. FIG. 1 shows an endoscope 1 as an insertion device. FIG. 2 shows a system in which the endoscope 1 is adopted. The endoscope 1 has a longitudinal axis C as shown in FIG. 1. One of directions parallel to the longitudinal axis C is defined as a distal direction (indicated by the arrow C1 in FIG. 1), and the other of the directions parallel to the longitudinal axis C is defined as a proximal direction (indicated by the arrow C2 in FIG. 1).

As shown in FIGS. 1 and 2, the endoscope 1 includes an elongated inserting section 2 extended along the longitudinal axis C, and a held section 3 provided to the proximal direction side of the inserting section 2. The inserting section 2 includes a distal rigid section 5, a bending section 6 provided to the proximal direction side with respect to the distal rigid section 5, and a flexible tube section 7 provided to the proximal direction side of the bending section 6. The bending section 6 is bendable in first bending directions (i.e., the directions indicated by the arrows L and R in FIG. 1) perpendicular to the longitudinal axis C. Furthermore, the bending section 6 is bendable in second bending directions (i.e., the directions indicated by the arrows U and D in FIG. 1) perpendicular to the longitudinal axis C and the first bending directions. In the present embodiment, the first bending directions are the bending LR directions, and the second bending directions are the bending UD directions. The flexible tube section 7 is elongated and flexible.

The held section 3 includes a held section casing 8 as an exterior. One end of a universal cord 10 is coupled to the held section 3. A scope connector 11 is provided to the other end of the universal cord 10. As shown in FIG. 2, the universal cord 10 is coupled to peripheral units, such as an image processing unit 12, a light source unit 13, a controlling unit 15, etc., via the scope connector 11. The image processing unit 12 is electrically connected to a display section 17 of a monitor, etc.

The distal rigid section 5 of the inserting section 2 is provided with an imaging element 19, such as CCD, etc. One end of an imaging cable 21 is connected to the imaging element 19. The other end of the imaging cable 21 is coupled to the image processing unit 12 via the scope connector 11 and the imaging cable pass through the inside of the held section casing 8 and the inside of the universal cord 10. In the inside of the inserting section 2, a light guide 23 configured to guide a light to be irradiated on an object is extended along the longitudinal axis C. The light guide 23 is connected to one end of a light guide tube 25 via the scope connector 11 and pass through the inside of the held section case 8 and the inside of the universal cord 10. The other end of the light guide tube 25 is connected to the light source unit 13.

Figure 3:
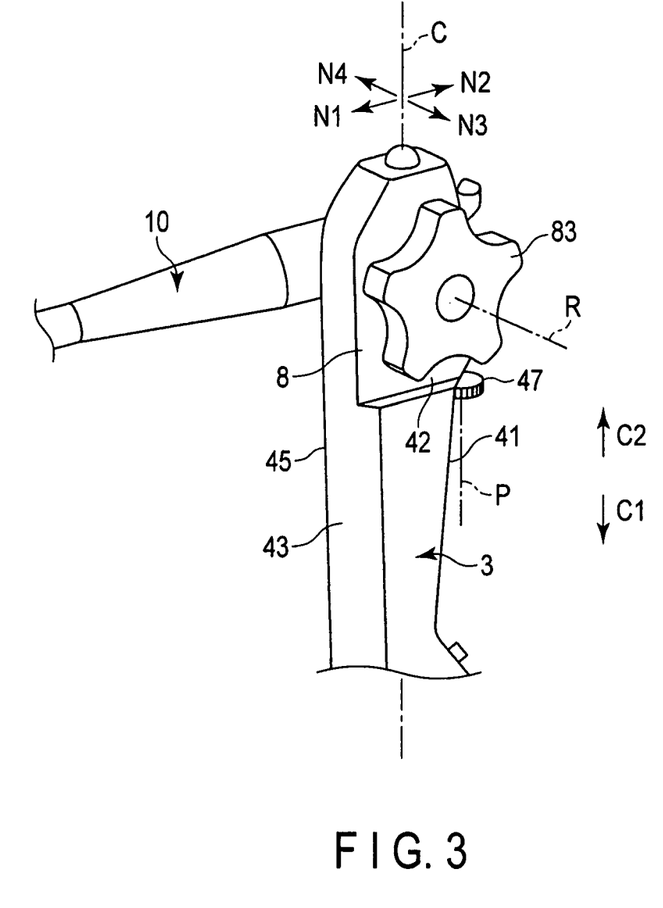
FIG. 3 is a perspective view schematically showing an exterior of the held section of the endoscope according to the present invention.
Figure 4:
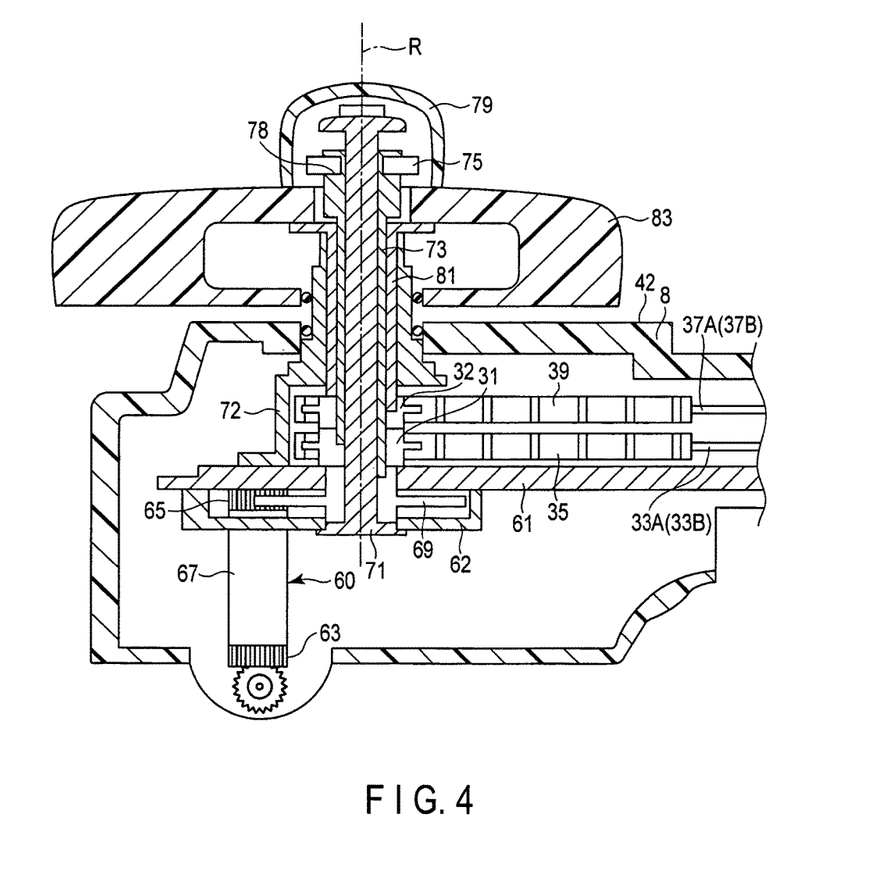
FIG. 4 is a sectional view schematically showing an internal configuration of the held section casing of the endoscope according to the first embodiment in a transmittable state.
Figure 5:
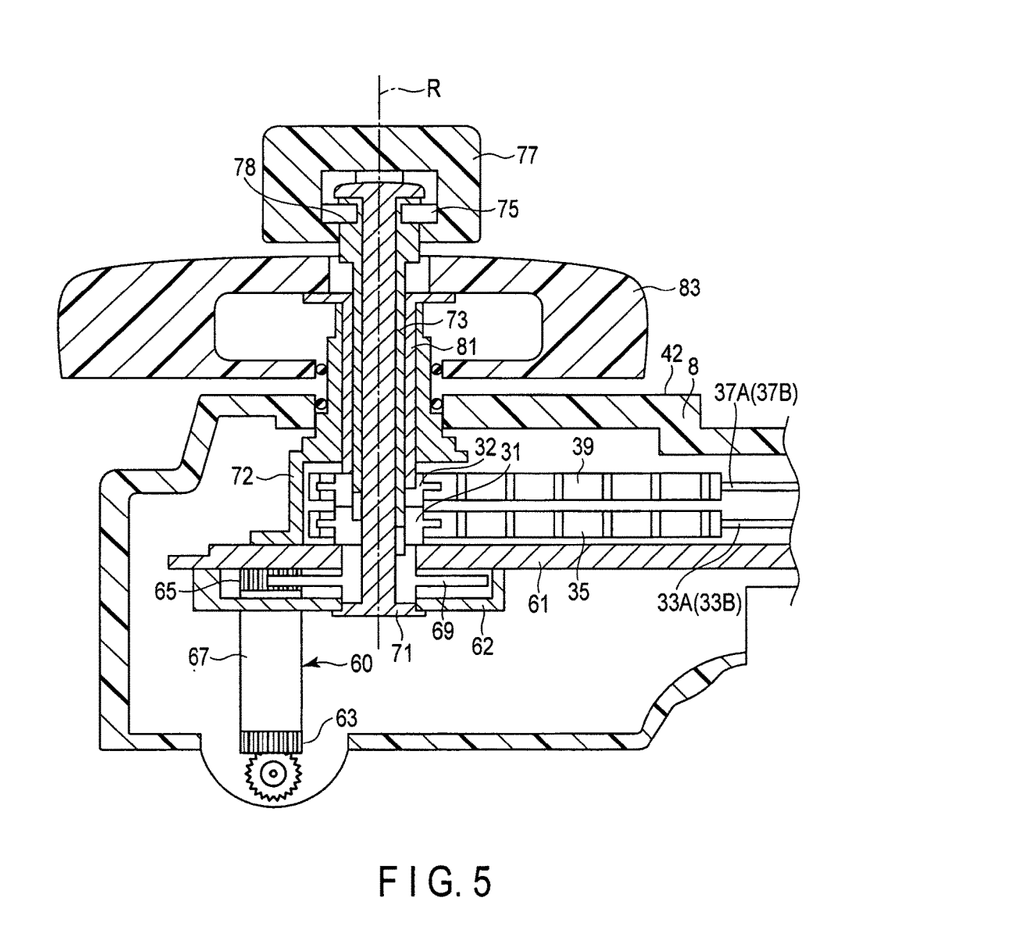
FIG. 5 is a sectional view schematically showing the internal configuration of the held section casing of the endoscope according to the first embodiment in a non-transmittable state.

FIG. 3 shows the exterior of the held section 3, and FIGS. 4 and 5 show the internal configuration of the held section casing 8. As shown in FIGS. 2, 4, and 5, in the inside of the held section case 8, an LR sprocket (a first rotating member) 31 and a UD sprocket (a second rotating member) 32 are provided (housed). The LR sprocket 31 and the UD sprocket 32 are rotatable about a rotational axis R which is perpendicular to the longitudinal axis C, and the LR sprocket 31 and the UD sprocket 32 are coaxial with respect to each other. The proximal ends of a pair of LR bending wires (first linear portions) 33A and 33B are connected to the LR sprocket 31 via an LR chain 35. The proximal ends of a pair of UD bending wires (second linear portions) 37A and 37B are connected to the UD sprocket 32 via a UD chain 39.

As shown in FIG. 2, the LR bending wires 33A and 33B are extended along the longitudinal axis C inside of the inserting section 2. The distal ends of the LR bending wires 33A and 33B are connected to a distal portion of the bending section 6. The LR sprocket (the first rotating member) 31 rotates about the rotational axis R so as to pull one of the LR bending wires 33A and 33B. For example, as the LR bending wire 33A is pulled, the bending section 6 is bent toward a bending Left direction (the direction indicated by the arrow L in FIG. 1), and as the LR bending wire 33B is pulled, the bending section 6 is bent in a bending Right direction (the direction indicated by the arrow R in FIG. 1). Thus, in the present embodiment, the bending section 6 is bent toward one of the bending LR directions, i.e., the first bending directions, when one of the LR bending wires (the first linear portions) 33A, 33B is pulled.

The UD bending wires 37A and 37B are extended along the longitudinal axis C inside of the inserting section 2. The distal ends of the UD bending wires 37A and 37B are connected to the distal portion of the bending section 6. The UR sprocket (the second rotating member) 32 rotates about the rotational axis R so as to pull one of the UD bending wires 37A or 37B. For example, as the UD bending wire 37A is pulled, the bending section 6 is bent toward a bending Up direction (the direction indicated by the arrow U in FIG. 1), and as the UD bending wire 37B is pulled, the bending section 6 is bent in a bending Down direction (the direction indicated by the arrow D in FIG. 1). Thus, in the present embodiment, the bending section 6 is bent toward one of the bending UD directions, i.e., the second bending directions, when one of the UD bending wires (the second linear portions) 37A, 37B is pulled.

Herein, as shown in FIG. 3, in the held section 3, one of the directions perpendicular to the longitudinal axis C and the rotational axis R is defined as a first perpendicular direction (indicated by the arrow N1 in FIG. 3), and the direction opposite to the first perpendicular direction is defined as a second perpendicular direction (indicated by the arrow N2 in FIG. 3). Also, a direction rotated 90 degrees from the first perpendicular direction toward a counterclockwise direction around the longitudinal axis C viewed from the proximal direction (the direction indicated by the arrow C2 in FIG. 3) is defined as a third perpendicular direction (indicated by the arrow N3 in FIG. 3), and the opposite direction to the third perpendicular direction is defined as a fourth perpendicular direction (indicated by the arrow N4 in FIG. 3). The third perpendicular direction and the fourth perpendicular direction are parallel to the rotational axis R. For example, the first and second perpendicular directions are parallel to the bending UD directions (the second bending directions) of the bending section 6 when the inserting section 2 is in a perfectly straight condition. For example, the third and fourth perpendicular directions are parallel to the bending LR directions (the first bending directions) of the bending section 6 when the inserting section 2 is in the perfectly straight condition.

The held section casing 8 includes a first exterior surface portion 41 facing toward the second perpendicular direction, and a second exterior surface portion 42 facing toward the third perpendicular direction. The held section casing 8 includes a third exterior surface portion 43 facing in the first perpendicular direction, and a fourth exterior surface portion 45 facing toward the fourth perpendicular direction. One end of the universal cord 10 is connected to the fourth external surface portion 45 and is extended from the fourth exterior surface portion 45 toward the first perpendicular direction.

A LR bending operation dial (electric bending operation section) 47 is provided to the first exterior surface portion 41. The LR bending operation dial 47 is rotatably coupled to the held section casing 8 about the rotational axis P with respect to the held section casing 8. The rotational axis P of the LR bending operation dial 47 is approximately parallel to the longitudinal axis C. The LR bending operation dial 47 rotates to input a LR electrical bending operation (electrical bending operation) for bending the bending section 6 in the bending LR directions.

As shown in FIG. 2, a potentiometer 48 is provided as a detecting section inside of the held section casing 8. One end of an electrical signal line 51 is connected to the potentiometer 48. The electrical signal line 51 is extended through the inside of the held section casing 8 and the inside of the universal cord 10. The control unit 15 is connected to the scope connector 11 via a wiring cable 52. Furthermore, the control unit 15 includes a driving control section 53. The other end of the electrical signal line 51 is connected to the driving control section 53 and the electrical signal line 51 is extended from the scope connector 11 through the inside of the wiring cable 52. The potentiometer 48 detects a rotation of the LR bending operation dial 47 so as to detect an input of the LR electrical bending operation by the LR bending operation dial 47. Then, an electrical signal based on the detection result is sent to the driving control section 53 via the electrical signal line 51.

An electric motor 55 as a driving member is provided inside the scope connector 11. The electric motor 55 is connected to the drive control unit 53 via the electric wiring 57. Upon inputting the LR electrical bending operation (electrical bending operation) in the LR bending operation dial (electric bending operation section), the driving control section 53 supplies an electric power to the electric motor 55 based on the detection result at the potentiometer 48. Upon being supplied with the electric power, the electric motor 55 is driven, and an electrical driving force is generated.

An actuating unit 60 is provided inside of the held section casing 8. A driving shaft 59 connects the actuating unit 60 to the electric motor 55. The driving shaft 59 is extended inside the universal cord 10. Upon driving the electric motor 55, an electrical driving force is transmitted to the actuating unit 60 via the driving shaft 59. The actuating unit 60 is actuated upon transmitting the electrical driving force.

Figure 6:
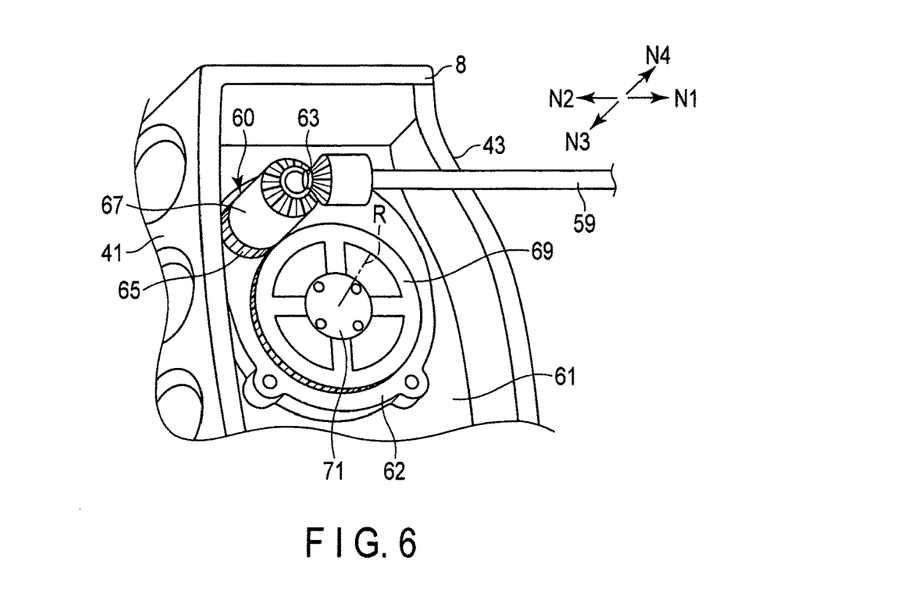
FIG. 6 is a perspective view schematically showing an actuating unit of the endoscope according to the first embodiment.

FIG. 6 shows the configuration of the actuating unit 60. As shown in FIGS. 4 to 6, a plate-shaped member 61 is fixed to the held section casing 8 inside the held section casing 8. A frame member 62 is fixed to the plate-like member 61. The actuating unit 60 includes a bevel gear 63 to which the driving shaft 59 is connected. The universal cord 10, in which the driving shaft 59 is internally extended, extends from the held section 3 toward the first perpendicular direction (upward direction perpendicular to the pages illustrating FIGS. 4 and 5, i.e., the direction indicated by the arrow N1 in FIG. 6). For this reason, the bevel gear 63 receives the electrical driving force from the first perpendicular direction via the driving shaft 59. Thus, in the present embodiment, the bevel gear 63 acts as a driving force receiving portion configured to receive the electrical driving force from the first perpendicular direction. Upon receiving the electrical driving force, the bevel gear 63 rotates.

The actuating unit 60 includes a relay gear 65. The relay gear 65 is attached to the plate-shaped member 61 in a manner such that the relay gear 65 is housed inside the frame member 62. A pillar-shaped member 67 couples the bevel gear 63 to the relay gear 65. Upon the rotation of the bevel gear 63, the electrical driving force is transmitted to the relay gear 65 via the pillar-like member 67, and the relay gear 65 pivots.

The actuating unit 60 includes a spur gear 69 that engages the relay gear 65. The spur gear 69 is coaxial with the LR sprocket 31 and the UD sprocket 32, and is rotatable about the rotational axis R. Upon the rotation of the relay gear 69, the electrical driving force is transmitted to the spur gear 69, and the spur gear 69 pivots.

A shaft member 71 is fixed to the frame member 62 inside the held section casing 8. Since the frame member 62 is fixed to the held section casing 8, the shaft member 71 is fixed to the held section casing 8. The shaft member 71 is coaxial with the LR sprocket 31 and the UD sprocket 32, and it is extended along the rotational axis R up to an outside of the held section casing 8 with penetrating the spur gear 69, the LR sprocket 31 and the UD sprocket 32. Accordingly, the spur gear 69, the LR sprocket 31, and the UD sprocket 32 are placed so as to cover an outer peripheral portion of the shaft member 71.

A cylindrical case 72 is fixed to the plate-shaped member 61 inside the held section casing 8. Since the plate-like member 61 is fixed to the held section casing 8, the cylindrical case 72 is fixed to the held section casing 8. The cylindrical case 72 is extended along the rotational axis R up to the outside of the held section casing 8. The LR sprocket 31 and the UD sprocket 32 are housed inside the cylindrical case 72.

A LR mantle 73 placed between the shaft member 71 and the cylindrical case 72 is extended along the rotational axis R up to the outside of the held section casing 8. The LR mantle 73 is attached to the LR sprocket 31 rotatably about the rotational axis R integrally with the LR sprocket (the first rotating member) 31. The LR toe 73 is movable with respect to the shaft member 71 and the LR sprocket 31 along the rotational axis R. In other words, the LR mantle 73 is a moving portion that is movable along the rotational axis R with respect to the LR sprocket 31.

A switching pin 75 which acts as a switch operation inputting section is fixed to the LR mantle 73 at the outside of the held section casing 8. A groove 78 is formed in the LR toe 73. The switching pin 75 is inserted in the groove 78, and the groove 78 and the switching pin 75 are engaged, thereby fixing the switching pin 75 to the LR mantle 73. Since the switching pin 75 is fixed to the LR mantle 73, an input of the switching operation by the switching pin 75 causes an operation force that results from the switching operation to be transmitted from a switching pin 75 to the LR mantle 73, which is a moving portion. As a result, the LR mantle 73 moves along the rotational axis R, and the connection state of the LR mantle 73 to the spur gear 69 of the actuating unit 60 is switched.

Upon switching the connection state of the LR mantle 73 to the actuating unit 60, the transmission state of the electrical driving force between the actuating unit 60 and the LR mantle 73 is switched, and the transmission state of the electrical driving force to the LR sprocket 31 is switched. Thus, the switching pin 75 and the LR mantle 73, which acts as a moving portion, both act as a connection switching section configured to switch the connection state of the LR mantle (moving portion) 73 to the actuating unit 60, and also act as a transmission switching section configured to switch the transmission state of the electrical driving force between the actuating unit 60 and the LR sprocket (the first rotating member) 31. The transmission state of the electrical driving force is switched to a transmittable state where an electrical driving force can be transmitted from the actuating unit 60 to the LR sprocket 31 (the state illustrated in FIG. 4), or to a non-transmittable state where an electrical driving force cannot be transmitted from the actuating unit 60 to the LR sprocket 31 (the state illustrated in FIG. 5). Thus, the LR mantle 73, which acts as the moving portion, moves when switching between the transmittable state and the non-transmittable state.

As shown in FIG. 4, in the transmittable state, the LR mantle 73 is connected to the spur gear 69 of the actuating unit 60. For this reason, the electrical driving force is transmitted to the LR mantle 73 upon the rotation of the spur gear 69, and the LR mantle 73 and the LR sprocket 31 integrally rotate about the rotational axis R.

On the other hand, as shown in FIG. 5, in the non-transmittable state, the LR mantle 73 is not connected to the spur gear 69 of the actuating unit 60. For this reason, an electrical driving force is not transmitted to the LR mantle 73 even when the spur gear 69 rotates, and therefore, the LR mantle 73 and the LR sprocket 31 do not rotate. Thus, under the non-transmittable state, the LR sprocket (the first rotational member) 31 does not rotate by the electrical driving force.

Under the non-transmittable state, an LR bending operation knob (a first manual bending operation section) 77 is detachably attached to the LR mantle (moving portion) 73 via the switching pin 75. The LR bending operation knob 77 is attached to the LR mantle 73 at the outside of the held section casing 8, thereby coupling the LR bending operation knob 77 to the held section casing 8. The LR bending operation knob 77 is coaxial with the LR mantle 73 when the LR bending operation knob 77 is attached to the LR mantle 73, and the knob 77 is rotatable about the rotational axis R integral with the LR mantle 73. Furthermore, while being coupled to the LR toe 73, the LR bending operation knob 77 is placed on the second exterior surface portion 42.

Under the non-transmittable state, the LR bending operation knob 77 is rotated to input an LR manual bending operation (a first manual bending operation) for bending the bending section 6 in the bending LR directions. Therefore, a first manual driving force is generated, and the first manual driving force is transmitted to the LR sprocket 31 via the switching pin 75 and the LR mantle 73. Upon transmitting the first manual driving force to the LR sprocket 31, the LR sprocket (first rotating member) 31 rotates integrally with the LR mantle (moving portion) 73. As previously mentioned, even under the non-transmittable state where no electrical driving force is transmitted from the actuating unit 60 to the LR sprocket 31, the first manual driving force generated by the input of the LR manual bending operation at the LR bending operation knob 77 is transmitted to the LR sprocket 31. For this reason, the LR sprocket 31 rotates by the first manual driving force.

It should be noted that, under the transmittable state, a cap 79, instead of the LR bending operation knob 77, is attached to the LR mantle 73. The cap 79 is detachably attached to the LR mantle 73 at the outside of the held section casing 8.

A UD mantle 81 located between the LR mantle 73 and the cylindrical case 72 is extended along the rotational axis R up to the outside of the held section casing 8. One end of the UD mantle 81 is coupled to the UP sprocket (second rotating member) 32, and the UD toe 81 is fixed to the UD sprocket 32. For this reason, the UD mantle 81 is rotatable about the rotational axis R integral with the UD sprocket 32.

At the exterior of the held section casing 8, a UD bending operation knob (second manual bending operation section) 83 is attached to the other end of the UD mantle 81, and the UD bending operation knob 83 is coupled to the held section casing 8. The UD bending operation knob 83 is fixed to the UD toe 81, and is rotatable about the rotational axis R integral with the UD mantle 81 and the UD sprocket 32. The UD bending operation knob 83 is placed on the second exterior surface portion 42. The shaft member 71 and the LR mantle 73 are extended with penetrating the UD bending operation knob 83.

Upon rotating the UD bending operation knob 83, a second UD manual bending operation (second manual bending operation) for bending the bending section 6 in the bending UD directions is input. Thus, a second manual driving force is generated, and the second manual driving force is transmitted to the UD sprocket 32 via the UD mantle 81. Upon transmitting of a second manual driving force to the UD sprocket 32, the UD sprocket (second rotating member) 32 rotates integrally with the UD mantle 81.

Next, the function and advantageous effects of the endoscope 1 according to the present embodiment are explained. When bending the bending section 6 toward one of the bending UD directions which are second bending directions, the UD bending operation knob 83 is rotated to input a UD manual bending operation (second manual bending operation). Thus, the second manual driving force is transmitted to the UD sprocket (second rotating member) 32 via the UD mantle 81, and the UD sprocket 32 rotates around the rotational axis R. Upon the rotation of the UD sprocket 32, one of the UD bending wires 37A or 37B is pulled, and the bending 6 is bent toward the bending Up direction or the bending Down direction.

In the endoscope 1, in a normal case where no malfunctions occur at the electric motor 55 which is a driving member, the LR mantle (moving portion) 73 is connected to the spur gear 69 of the actuating unit 60. For this reason, the endoscope 1 is then in the transmittable state where an electrical driving force from the electric motor 55 is transmitted from the actuating unit 60 to the LR sprocket (first rotating member) 31.

In the normal state where no malfunction occurs at the electric motor 55, the LR bending operation dial (electric bending operation section) 47 is rotated to input the LR electrical bending operation (electrical bending operation). Then, the driving control section 53 supplies electric power to the electric motor 55 based on the detection result at the potentiometer 48. Upon being supplied with electric power, the electric motor 55 is driven, and an electrical driving force is generated. Then, upon transmitting the electrical driving force to the actuating unit 60, the actuating unit 60 is actuated.

In the transmittable state, the electrical driving force can be transmitted from the actuating unit 60 to the LR sprocket 31. For this reason, the LR sprocket 31 rotates about the rotational axis R upon actuating the actuating unit 6. As the LR sprocket 31 rotates, one of the LR bending wires 33A or 33B is pulled, and the bending 6 is bent toward the bending Right direction or the bending Left direction.

When any malfunctions occur at the electric motor 55, the LR mantle (moving portion) 73 is moved from the transmittable state along the rotational axis R by the switching operation at the switching pin 75. As a result, the LR mantle 73 is not connected to the spur gear 69 of the actuating unit 60, and is in the non-transmittable state where no electric moving force is transmitted from the actuating unit 60 to the LR sprocket 31. At this time, even when the LR electrical bending operation is input at the LR bending operation dial 47, and the actuating unit 60 is actuated, the LR sprocket 31 does not rotate by the electrical driving force.

Furthermore, under the non-transmittable state, the cap 79 is removed from the LR toe 73, and the LR bending operation knob (first manual bending operation section) 77 is detachably attached to the LR mantle 73. At this time, upon rotating the LR bending operation 77, the LR manual bending operation (first manual bending operation) is input. As a result, a manual driving force is transmitted to the LR sprocket (first rotating member) 73 via the LR mantle 73, and the LR sprocket 31 rotates about the rotational axis R. As the LR sprocket 31 rotates, one of the LR bending wires 33A or 33B is pulled, and the bending 6 is bent toward the bending Right direction or the bending Left direction.

As previously mentioned, when any malfunction occurs at the electric motor 55 which is a driving member, the endoscope 1 is switched into the non-transmittable state where no electrical driving force is transmitted from the actuating unit 60 to the LR sprocket 31. For this reason, it is possible to eliminate the influence of malfunctions on the bend of the bending section 6.

Moreover, under the non-transmittable state, an LR bending operation knob 77 is attached to the LR mantle 73. Upon input of the LR manual bending operation at the LR bending operation knob 77, a manual driving force is transmitted to the LR sprocket 31, and the LR sprocket 31 rotates about the rotational axis R. By the rotation of the LR sprocket 31, the bending 6 is bent toward one of the bending LR directions (first bending directions). Accordingly, it is possible to bend the bending section 6 appropriately without driving the electric motor 55, even when any malfunction occurs at the electric motor 55.

Furthermore, at the endoscope 1, in order to realize the switching of the state of transmission of the electrical driving force from the actuating unit 60 to the LR sprocket 31, the LR mantle 73 is enabled to move along the rotational axis R with respect to the LR sprocket 31, and the switching pin 75 is provided to the LR mantle 73. In other words, the switching of the state of transmission of the electrical driving force can be realized without making the configuration of the interior of the held section casing 8 complicated.

At the endoscope 1, as the LR bending operation knob 77 is detachably attached to the movable LR mantle 73, it is possible to input the LR manual bending operation (first manual bending operation) under the non-transmittable state. In other words, it is possible to input the LR manual bending operation under the non-transmittable state without making the configuration of the held section 3 complicated.

Figure 7:
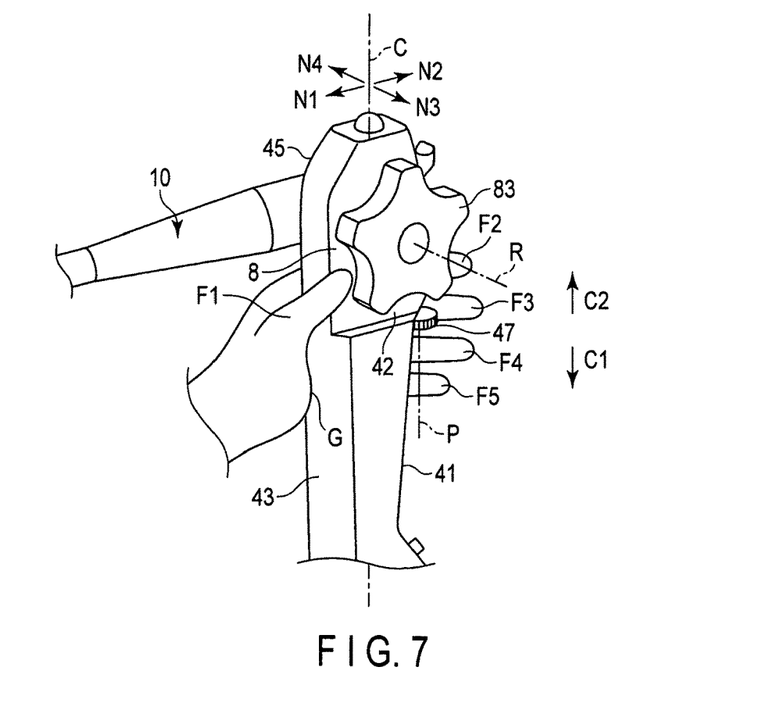
FIG. 7 is a perspective view schematically showing the held section of the endoscope according to the first embodiment when it is held by an operator's left hand.

FIG. 7 shows the held section 3 held by an operator with their left hand. As shown in FIG. 7, while the held section 3 is being held, the palm G is touching the third exterior surface portion 43 facing toward the first perpendicular direction (indicated by the arrow N1 in FIG. 7). Also, at the fourth exterior surface portion 45 facing toward the fourth perpendicular direction (indicated by the arrow N4 in FIG. 7), the index finger F2, the middle finger F3, the ring finger F4 and the little finger F5 are extended from the first perpendicular direction toward the second perpendicular direction (indicated by the arrow N2 in FIG. 7).

Accordingly, it becomes easier for the operator to hold the held section 3 by configuring the actuating unit 60 to receive an electrical driving force from the first perpendicular direction. Furthermore, it becomes easier for the operator to input the LR electrical bending operation by the LR bending operation dial 47 with the index finger F2 or the middle finger F3 while holding the held section 3 by arranging the LR bending operation dial 47 on the first exterior surface portion 41 which faces toward the second perpendicular direction. Furthermore, as the LR bending operation knob 77 and the UD bending operation knob 83 are placed on the second exterior surface portion 42 facing toward the third perpendicular direction (indicated by the arrow N3 in FIG. 7), it becomes easier for the operator to input the LR manual bending operation by the LR bending operation knob 77 with the thumb F1, and to input the UD manual bending operation by the UD bending operation knob 83 with the thumb, while holding the held section 3.

(Modifications)

In the aforementioned embodiment, the connection of the LR mantle 73, which is coaxial with the rotational axis R, to the actuating unit 60 is switched in order to switch between the transmittable state and the non-transmittable state; however, the way of switching between the states is not limited thereto. For example, as a modification, a spur gear (not shown) may be provided to the actuating unit 60 and a gear section (not shown) provided to the LR sprocket 31, so that the engagement of the spur gear of the actuating unit 60 and the gear section of the LR sprocket 31 can be changed. In this case, when the spur gear of the actuating unit 60 and the gear section of the LR sprocket 31 are engaged, the endoscope will be in the transmittable state. When the spur gear is moved from the transmittable state and the spur gear does not engage the gear section of the LR sprocket 31, the endoscope will be in the non-transmittable state.

Furthermore, in the aforementioned embodiment, an electric bending operation section for inputting the LR electrical bending operation is the LR bending operation dial 47; however, it is not limited thereto. For example, the electric bending operation section may be an LR bending operation lever.

Furthermore, in the aforementioned embodiment, a configuration of switching the state of transmitting an electrical driving force to the LR sprocket 31 when bending the bending section 6 in the bending LR directions is described; however, such a configuration is not limited thereto. For example, when bending the bending section 6 in the bending UD directions, an electrical driving force can be generated at a driving member (not shown), and the state of transmitting the electrical driving force to the UD sprocket 32 can be switched. Furthermore, in the aforementioned embodiment, the electric motor 55, which is a driving member, is provided in the scope connector 11; however, the location to place the driving member is not limited thereto. For example, an electric driving member may be detachably attached to the held section 3.

Furthermore, in the aforementioned embodiment, the endoscope 1 was explained; however, the embodiment can be realized in a different device. For example, the aforementioned configuration can be applied to a manipulator having an inserting section in which a bending section is provided, the bending section being bendable in the first bending directions perpendicular to the longitudinal axis and bendable in the second bending directions perpendicular to the first bending direction. In other words, the previously-mentioned configuration may be applied to an insertion device, such as the endoscope 1, etc.

Thus, in an insertion device, such as the endoscope 1, the actuating unit 60, which is actuated by an electrical driving force generated by a driving member (55), should be provided inside the held section casing 8. Furthermore, a transmission switching section (75) configured to switch the states of transmission of the electrical driving force from a driving member (55) between the actuating unit 60 and a first rotating member (31) should be provided. The transmission switching section (75) should switch between the non-transmittable state where no electrical driving force is transmitted from the actuating unit 60 to a first rotating member (31) and the transmittable state where the electrical driving force is transmitted from the actuating unit 60 to a first rotating member (31) to rotate the first rotating member (31).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion device comprising:
an inserting section which is extended along a longitudinal axis;
a bending section which is provided to the inserting section, and which is bendable in first bending directions and in second bending directions which are different from the first bending directions;
a first rotating member which is configured to rotate to bend the bending section toward one of the first bending directions;
a driving member which is configured to generate an electrical driving force upon being supplied with an electric power;
an actuating unit which is configured to be actuated upon transmitting the electrical driving force generated in the driving member to the actuating unit;
a second rotating member which is coaxially arranged with a rotational axis of the first rotating member, and which is configured to rotate about the rotational axis to bend the bending section toward one of the second bending directions;
a held section casing provided to a proximal direction side of the inserting section, the first rotating member and the second rotating member being arranged inside the held section casing; and
a moving member which is arranged inside the first rotating member and the second rotating member along the rotational axis, and which is movable between a first state and a second state, the moving member being connected to both the second rotating member and the actuating unit in the first state so that the electrical driving force is transmitted from the actuating unit to the second rotating member through the moving member when the driving member generates the electrical driving force, the moving member being connected to the second rotating member but being not connected to the actuating unit in the second state so that the electrical driving force is not transmitted to the second rotating member from the actuating unit even when the driving member generates the electrical driving force, the moving member being configured to rotate integrally with the second rotating member about the rotational axis in both the first state and the second state when the second rotating member rotates,
wherein the moving member extends to an outside of the held section casing and is configured to receive an operation force from the outside of the held section casing so that the moving member moves longitudinally along the rotational axis between the first and second states.

2. The insertion device according to claim 1, wherein the moving member includes a switching operation inputting section provided outside of the held section casing and configured to move the moving member along the rotational axis.

3. The insertion device according to claim 2, wherein the switching operation inputting section is configured to move the moving member between a position in the first state and a position in the second state.

4. The insertion device according to claim 3, further comprising a shaft member which is extended along the rotational axis, and which is coaxially arranged with the first rotating member and the second rotating member, the moving member being located to an outer peripheral side of the shaft member.

5. The insertion device according to claim 4, wherein the actuating unit includes a connecting section which is coaxially arranged with the first rotating member, the second rotating member, and the shaft member, and
the connecting section is arranged in a manner so as to cover an outer peripheral of the shaft member.

6. The insertion device according to claim 2, further comprising:
a first manual bending operation section which is capable of inputting a first manual bending operation,
wherein:
the manual bending operation section is configured to transmit a first manual driving force to the second rotating member via the moving member by an input in the first manual bending operation section under the second state so as to rotate the second rotating member, and
the first manual driving force is transmitted from the first manual bending operation section to the moving member outside of the held section casing.

7. The insertion device according to claim 6, wherein
the first manual bending operating section is detachably attached to the moving member via the switching operation inputting section under the second state, and
upon the input of the first manual bending operation, the first manual bending operating section is configured to rotate about the rotational axis so as to rotate the moving member and the second rotating member integrally by the first manual driving force.

8. The insertion device according to claim 7, further comprising:
a second manual bending operation section which is coupled to the held section casing, and which is capable of inputting a second manual bending operation, upon an input of the second manual bending operation, the second manual bending operation section being configured to transmit a second manual driving force to the first rotating member so as to rotate the first rotating member.

9. The insertion device according to claim 8, wherein the second manual bending operating section is configured to rotate about the rotational axis by the input of the second manual bending operation, and configured to rotate the first rotating member by the second manual driving force.

10. The insertion device according to claim 9, further comprising an electric bending operation section which is coupled to the held section casing, and which is capable of inputting an electrical bending operation, under the first state, the electric bending operation section being configured to supply the electric power to the driving member upon an input of the electric bending operation, and configured to rotate the second rotating member.

11. The insertion device according to claim 10, wherein:
the actuating unit includes a driving force receiving portion which is configured to receive the electrical driving force from the first perpendicular direction perpendicular to the longitudinal axis of the inserting section and perpendicular to the rotational axis, and
the held section casing includes a first exterior surface portion on which the electric bending operation section is placed, and which faces toward a second perpendicular direction opposite to the first perpendicular direction.

12. The insertion device according to claim 11, wherein the held section casing includes a second exterior surface portion which faces toward a third perpendicular direction which is counterclockwise rotated for an angle of 90 degrees from the first perpendicular direction around the longitudinal axis viewed from a proximal direction, the first manual bending operation section and the second manual bending operation section being arranged on the second exterior surface portion.

* * * * *

UNITED STATES PATENT AND TRADEMARK OFFICE
CERTIFICATE OF CORRECTION

| | |
|---|---|
| PATENT NO. | : 10,194,786 B2 |
| APPLICATION NO. | : 14/479810 |
| DATED | : February 5, 2019 |
| INVENTOR(S) | : Yutaka Masaki |

Page 1 of 1

It is certified that error appears in the above-identified patent and that said Letters Patent is hereby corrected as shown below:

On the Title Page

The following information should be added:

Related U.S. Application Data
(63)  Continuation of Application No. PCT/JP2014/052625, filed on February 5, 2014.

(30)  Foreign Application Priority Data
February 5, 2013 (JP) ..................................... 2013-020726

Signed and Sealed this
Twenty-eighth Day of April, 2020

Andrei Iancu
*Director of the United States Patent and Trademark Office*